(12) United States Patent
Weimer et al.

(10) Patent No.: US 7,396,862 B2
(45) Date of Patent: Jul. 8, 2008

(54) DENTAL COMPOSITE FILLER PARTICLES

(76) Inventors: Alan W. Weimer, 6967 Springhill Dr., Niwot, CO (US) 80503; Sotiris E. Pratsinis, Aurorastrasse 73, CH-8032, Zurich (CH) 8032; Christos Angeletakis, 716 W. Brentwood Wood, Orange, CA (US) 92865; Steven M. George, 1444 Cassin Ct., Boulder, CO (US) 80303

(*) Notice: Subject to any disclaimer, the term of this patent is extended or adjusted under 35 U.S.C. 154(b) by 517 days.

(21) Appl. No.: 10/773,685

(22) Filed: Feb. 6, 2004

(65) Prior Publication Data
US 2004/0224087 A1    Nov. 11, 2004

Related U.S. Application Data

(60) Provisional application No. 60/445,540, filed on Feb. 6, 2003.

(51) Int. Cl.
*A61K 6/083* (2006.01)
*B32B 18/00* (2006.01)
*B32B 19/00* (2006.01)

(52) U.S. Cl. .............. 523/116; 523/115; 106/401; 428/404

(58) Field of Classification Search ............ 523/116; 427/453, 585; 428/404
See application file for complete search history.

(56) References Cited

U.S. PATENT DOCUMENTS

| 4,503,169 | A | 3/1985 | Randklev | |
| 6,235,270 | B1 * | 5/2001 | Ishii et al. | 424/59 |
| 6,254,940 | B1 | 7/2001 | Pratsinis et al. | |
| 6,572,693 | B1 | 6/2003 | Wu et al. | |
| 6,613,383 | B1 | 9/2003 | George et al. | |
| 6,648,958 | B2 * | 11/2003 | Anselmann et al. | 106/442 |
| 6,899,948 | B2 * | 5/2005 | Zhang et al. | 428/331 |
| 6,913,827 | B2 * | 7/2005 | George et al. | 428/402 |

FOREIGN PATENT DOCUMENTS

WO    WO 03/008186 A1    1/2003

OTHER PUBLICATIONS

J.D. Ferguson et al., "TiO2 Atomic Layer Deposition on ZrO2 Particles Using Alternating Exposures of TiCl4 and H2O", Applied Surface Science, 12 pages (2004).

Derek W. Jones, "Detal Composite Biomaterial", J. Can. Dent. Assoc., 8 pages (1998).

"Detal and Medical Materials", Polymers Technical Activities, 24 pages (1997).

* cited by examiner

*Primary Examiner*—Tae H. Yoon
(74) *Attorney, Agent, or Firm*—Gary C. Cohn PLLC

(57) ABSTRACT

Dental composite filler materials comprise particles coated via an atomic layer deposition (ALD) process. The coating material has a different composition than the core particle. The difference in composition permits fine control over the refractive index of the coated particles, allowing good matching tooth enamel and to the binder materials used in the composite.

7 Claims, No Drawings

DENTAL COMPOSITE FILLER PARTICLES

CROSS-REFERENCE TO RELATED APPLICATION

This application claims benefit under 35 USC §119 of provisional application 60/445,540, filed Feb. 6, 2003, incorporated herein by reference in its entirety.

BACKGROUND OF THE INVENTION

This invention relates to filler materials for dental composites and to dental composites containing such filler materials.

So-called amalgam dental fillings are being increasingly replaced with dental composites that more closely match the color and appearance of the natural tooth. These composites generally consist of an organic resin that contains a microparticle filler. Most systems incorporate a light- or UV-curable polymeric resin, such as a diglycidylmethacrylate of bisphenol A (BIS-GMA), triethyleneglycol dimethacrylate (TEGDMA) or a urethane dimethacrylate (UDMA). The filler particles are typically barium silicate glass, quartz or zirconium silicate, combined with small colloidal silica particles.

To match the appearance of the original tooth enamel and provide a natural, tooth-like appearance, the inorganic particles must be translucent and display minimal light scattering. The composite of inorganic particles and polymeric resin must have a refractive index in the range of about 1.48 to 1.60, especially ~1.54. Both the resin and the filler particles should have very nearly the same refractive index, to minimize light scattering. Polymeric resins can be blended to achieve this refractive index. Obtaining the necessary refractive index for the filler particles is more problematic.

One approach to producing filler particles of the required refractive index is described in U.S. Pat. No. 4,503,169 to Randklev. Randklev produces microparticles containing amorphous silica microregions interspersed with polycrystalline ceramic metal oxide microregions. Silica ($SiO_2$) is a very low cost inorganic material having a refractive index of ~1.46. The ceramic metal oxide used in Randklev's process is preferably zirconia ($ZrO_2$), which has a refractive index of about 2.20, because $ZrO_2$ has the added benefit of being opaque to x-ray radiation. Microparticles having any refractive index between that of silica and that of zirconia can be produced in Randklev's process by varying the relative proportions of these components, provided that crystalline microregions having diameters of greater than about 400 microns (the shortest wavelength of visible light) are excluded. In Randklev's process, $ZrO_2$ is mixed with $SiO_2$ using sol-gel techniques to form the microparticle composites. One of the problems with the sol-gel process is that the starting materials must be blended carefully and then temperature processed to obtain the composite microparticles. This processing is variable and can lead to voids in the composite microparticle. These voids scatter light and increase the opacity. Large crystallites of $ZrO_2$ that form during the thermal processing also lead to light scattering. This seriously degrades the appearance of the composite. In addition, there is very little control over the resulting refractive index of the dental composite when using these composite microparticles.

It would therefore be desired to produce a filler material for dental composites, which has a carefully controlled refractive index and exhibits a desirable opacity and minimal light scattering.

SUMMARY OF THE INVENTION

In one aspect, this invention is a material in the form of particles having an average diameter of up to about 350 nanometers, the particles comprising a base particle having an average diameter of up to about 300 nanometers and one or more coating layers on the surface of said base particle, wherein said base particle or at least one coating layer is silica ($SiO_2$), and said base particle or at least one coating layer is a metal oxide having a refractive index greater than 1.60, wherein the particles have a predetermined refractive index greater than that of silica alone.

In another aspect, this invention is curable dental composite material comprising a light-curable polymeric resin and a particulate filler material, wherein the particulate filler material includes particles as described in the first aspect that have a refractive index in the range of about 1.48 to about 1.60.

In a third aspect, this invention is a process for making a filler material having a predetermined refractive index, which comprises applying, by an atomic layer deposition process, one or more coating layers to a base particle having an average diameter of up to about 300 nanometers to form a coated particle having an average diameter of up to about 350 nanometers, wherein said base particle or at least one coating layer is silica ($SiO_2$), and said base particle or at least one coating layer is a metal oxide having a refractive index greater than 1.60, wherein the particles have a predetermined refractive index greater than that of silica alone.

DETAILED DESCRIPTION OF THE INVENTION

The coated particles of the invention have an average diameter of up to about 350 nanometers, preferably up to about 200 nanometers, more preferably up to about 150 nanometers and especially up to about 125 nanometers. The preferred smaller particles do not scatter light as much as the larger ones. The coated particles may be as small as about 10 nanometers, preferably as small as about 20 nanometers in diameter. Most typically, the coated particles will have an average diameter of about 30-100 nanometers, especially from about 30-80 nanometers.

The particles are made up from a base particle that is coated with one or more coating layers. The base particle or at least one of the coating layers is silica. If the base particle is not silica, it is of one or more metal oxides as described below. When the base particle is silica, one or more of the coating layers is such a metal oxide.

The metal oxide is characterized by having a refractive index of greater than 1.60, by being non-toxic as used in the dental composite, and by being colorless or only weakly colored. The refractive index of the metal oxide is preferably greater than about 2.0. Examples of suitable metal oxides are $BaO$, $Bi_2O_3$, $CaO$, $Nb_2O_3$, $SnO_2$, $Ta_2O_3$, $TiO_2$, $Y_2O_3$, $ZnO$, $ZrO_2$, $CeO_2$, $Ce_2O_3$ and $La_2O_3$. $ZrO_2$ and $TiO_2$ are preferred. $ZrO_2$ has a refractive index of approximately 2.20. $TiO_2$ has a refractive index of ~2.49 when in an anatase crystalline phase and of ~2.90 when in a rutile crystalline phase. $TiO_2$ coatings in this invention may be made in rutile or anatase crystalline forms, and in an apparently amorphous form as well, depending on conditions used to make the coating. The $TiO_2$ may also exist partially in a crystalline form and partially in an amorphous form. As discussed below, $ZrO_2$ and $TiO_2$ can be used to form separate coating layers on the base particle.

The refractive index of the particle of the invention varies approximately linearly between the refractive index of the silica and that of the metal oxide(s). The refractive index can be approximately predicted by interpolation based on a comparison of the relative volume percent of the silica and the metal oxide in the particle. This relationship allows for good prediction of particle refractive index provided that the particle is significantly smaller than about 350 nanometers and is relatively free of agglomerations and crystalline domains larger than about 350 nanometers. These estimates are useful for determining the approximate coating thicknesses needed to obtain the desired refractive index for the coated particle. For these dental applications, the refractive index of the coated particle is generally between 1.47 and 1.75, preferably between 1.48 and 1.60, and especially between 1.50 and 1.58. A refractive index of 1.54±0.01 is most preferred.

For example, the refractive index of 60 nanometer diameter silica particles can be adjusted into the range of 1.50-1.60 by applying a $ZiO_2$ coating of about 1.4 to about 4 nm thickness. A $ZiO_2$ coating of about 2.3 nm on such silica particles results in a refractive index of about 1.54. A rutile $TiO_2$ coating of about 0.6 to about 2 nm thickness is sufficient to raise the refractive index of 60 nm diameter silica particles to 1.50 to 1.60. A $TiO_2$ coating thickness of about 1.18 nm adjusts the refractive index to about 1.54.

Refractive index of the particles is conveniently measured using turbidity methods, by placing the particles in suspension and comparing them with a standard suspension such as formazine (refractive index=1.85), using a turbidimeter. A suitable turbidimeter is a LabScat Dual-Angle Lab Turbidimeter, available from Sigrist-Photometer AG. Alternatively, Mie scattering simulations can be used to ascertain refractive index, as described by Aden and Kerker, "Scattering of electromagnetic waves from two concentric spheres", *J. Appl. Phys.* 22, 1242-1246 (1951) and by Toon & Ackerman, "Algorithm for the calculation of scattering by stratified spheres", *Appl. Opt.* 20, 3657-3660 (1981).

Various different combinations of silica and metal oxide can be prepared, such as:

a) Silica base particle with one or more layers of a metal oxide. The metal oxide is preferably $ZrO_2$ or $TiO_2$. A $ZrO_2$ layer has the additional advantage, relative to $TiO_2$, of making the particle radiopaque. $TiO_2$ layers may be amorphous or in a rutile or anatase crystalline form, or exist as a mixture of such forms. Coating thicknesses will depend on the diameter of the base particle, but in general will be from about 0.5 to about 50 nanometers, especially from about 1 to about 20 nanometers, and in particular from about 1 to about 10 nanometers.

b) Silica base particle with two or more layers of different metal oxides. Preferred particles having this construction include silica particles having one or more $TiO_2$ layers which are in turn coated with one or more $ZrO_2$ layers. Because of the higher refractive index of $TiO_2$, (relative to $ZrO_2$), less of it is needed on a volume basis to raise the refractive index of the particle to the desired value. A thin $TiO_2$ layer can therefore be applied to raise the particle refractive index to close to the desired value, and a thin $ZrO_2$ layer can be applied atop the $TiO_2$ layer to fine-tune the refractive index and provide radiopacity. An outer $ZrO_2$ layer on the $TiO_2$ layer provides a harder shell. A $TiO_2$ layer interposed between a silica base particle and an outer $ZrO_2$ layer provides an added benefit of improving the bond between the $ZrO_2$ layer and the particle. Silica particles having a $TiO_2$ layer atop an underlying $ZrO_2$ layer are also within the scope of the invention. The metal oxide coating layers will have thicknesses as described under a) above.

c) $ZrO_2$ base particles having a $SiO_2$ coating layer. The $ZrO_2$ base particles provide radiopacity and increase the refractive index (relative to the $SiO_2$). The $SiO_2$ layer is thick enough to reduce the particle refractive index to the desired value. It also tends to make the particles more easily dispersible in the resin. The $SiO_2$ layer is generally about 1-100 nm, preferably from about 5-80 nm in thickness, although this will depend on the radius of the $ZrO_2$ base particle and the desired refractive index.

d) $TiO_2$ base particles having one or more $SiO_2$ coating layers, optionally also including one or more $ZrO_2$ layers beneath and/or on top of the $SiO_2$ layer(s). Layer thicknesses are chosen to provide the desired refractive index, as before, and the $ZrO_2$ layer provides radiopacity. An $SiO_2$ layer is generally about 1-100 nm, preferably from about 5-80 nm in thickness, although this will depend on the radius of the $ZrO_2$ base particle and the desired refractive index. $ZrO_2$ layer thickness will generally be as described in a) above.

Radiopacity equal to or greater than that of 1 mm of aluminum, especially equal or greater to that of 2 mm of aluminum, is preferred. For this reason, it is highly preferred that the base particle or at least one coating layer is a radiopaque material, especially $ZrO_2$.

A silica outermost coating is desirable in all cases to provide improved dispersability in the resin. This coating will of course affect the refractive index of the particle and its thickness must be taken into account together with those of the base particle and other layers to achieve the desired refractive index. Outermost silica coatings of about 1 to about 20 nm are particularly suitable.

The particulate is preferably non-agglomerated after the coating is deposited. By "non-agglomerated", it means that the particles do not form significant amounts of agglomerates during the process of coating the substrate particles. Particles are considered to be non-agglomerated if (a) the average particle size does not increase more than about 5%, preferably not more than about 2%, more preferably not more than about 1% (apart from particle size increases attributable to the coating itself) as a result of depositing the coating, or (b) if no more than 2 weight %, preferably no more than 1 weight % of the particles become agglomerated during the process of depositing the inorganic material.

The particle coating layers are preferably conformal. By "conformal" it is meant that the thickness of the coating layer is relatively uniform across the surface of the particle (so that, for example, the thickest regions of the coating are no greater than 3× the thickness of the thinnest regions), so that the surface shape of the coated substrate closely resembles that of the underlying substrate surface. Conformality is determined by methods such as transmission electron spectroscopy (TEM) that have resolution of 10 nm or below. Lower resolution techniques cannot distinguish conformal from non-conformal coatings at this scale. The desired substrate surface is preferably coated substantially without pinholes or defects.

The coating layers are advantageously deposited in an Atomic Layer Deposition (ALD) process, using the base particles as a substrate. A suitable ALD process for depositing nanocoatings on fine particles is described in U.S. Pat. No. 6,613,383 and WO 03/008186A1. In the ALD process, the coating-forming reaction is conducted as a series of (typically two) half-reactions. In each of these half-reactions, a single reagent is introduced into contact with the substrate particle surface under conditions such that the reagent is in the form of a gas. The reagent reacts with functional groups on the surface of the particle and becomes bound to the particle. Excess amounts of the reagent are removed, which helps to prevent the growth of undesired, larger inclusions of the coating material. Each remaining half-reaction is then conducted in turn, each time introducing a single reagent, allowing it to react at the surface of the particle, and removing excess reactant before introducing the next reagent. Usually, a carrier gas is used to introduce the reagents, and the reaction chamber is swept with the carrier gas between successive reagent introductions to help remove excess reagents and gaseous reaction products. Also, in some instances a precursor reaction may be done to introduce desirable functional groups onto the surface of the underlying particle, to provide a mechanism for covalent bonding of the coatings to the particle (or an underlying deposited layer).

Atomic layer controlled growth techniques permit the deposition of coatings of up to about 0.4 nm in thickness per reaction cycle, and thus provide a means of extremely fine control over coating thickness. Film thickness for preferred $ZrO_2$ and $TiO_2$ films is often controllable to about 0.1-0.2 nm/reaction cycle. Thicker coatings can be prepared by repeating the reaction sequence to sequentially deposit additional layers of the coating material until a desired coating thickness is achieved.

A convenient method for applying the coating to the base particles is to form a fluidized bed of the particles, and then pass the various reagents in turn through the fluidized bed under reaction conditions. Methods of fluidizing particulate materials are well known, and generally include supporting the particles on a porous plate or screen. A fluidizing gas is passed upwardly through the plate or screen, lifting the particles somewhat and expanding the volume of the bed. With appropriate expansion, the particles behave much as a fluid. Fluid (gaseous or liquid) reagents can be introduced into the bed for reaction with the surface of the particles. In this invention, the fluidizing gas also can act as an inert purge gas for removing unreacted reagents and volatile or gaseous reaction products.

In addition, the reactions can be conducted in a rotating cylindrical vessel or a rotating tube. This method is particularly suitable for continuous processes.

Of particular interest in this invention are ALD reactions for depositing $ZrO_2$, $TiO_2$ and $SiO_2$ layers atop underlying particulate substrates.

Oxide coatings, including $ZrO_2$, $TiO_2$ and $SiO_2$ coatings, can be prepared on particles having surface hydroxyl or amine (M-N-H) groups using a binary (AB) reaction sequence as follows. The asterisk (*) indicates the atom that resides at the surface of the particle or coating, and Z represents oxygen or nitrogen from the surface hydroxyl or amine group. $M^1$ is an atom of a metal (or semimetal in the case of silicon), and X is a displaceable nucleophilic group. The reactions shown below are not balanced, and are only intended to show the reactions at the surface of the particles (i.e., not inter- or intralayer reactions).

$$\text{M-Z-H*} + M^1X_n \rightarrow \text{M-Z-}M^1\text{X*} + \text{HX} \tag{A1}$$

$$\text{M-Z-}M^1\text{X*} + H_2O \rightarrow \text{M-Z-}M^1\text{OH*} + \text{HX} \tag{B1}$$

In reaction A1, reagent $M^1X_n$ reacts with one or more M*-Z-H groups on the surface of the particle to create a new surface group having the form -$M^1$-X. $M^1$ is bonded to the particle through one or more Z (nitrogen or oxygen) atoms. The -$M^1$-X group represents a site that can react with water in reaction B1 to regenerate one or more hydroxyl groups. The surface hydroxyl groups formed in reaction B1 can serve as functional groups through which reactions A1 and B1 can be repeated, each time adding a new layer of $M^1$ atoms. Note that hydroxyl groups can be eliminated as water, forming $M^1$-O-$M^1$ bonds within or between layers. This condensation reaction can be promoted if desired by, for example, annealing at elevated temperatures and/or reduced pressures.

For $TiO_2$, a preferred binary reaction sequence is:

$$\text{M-Z-H*} + TiCl_4 \rightarrow \text{M-Z-TiCl}_3\text{*} + \text{HCl} \tag{A2}$$

$$\text{M-Z-TiCl*} + H_2O \rightarrow \text{M-Z-TiOH*} + \text{HCl} \tag{B2}$$

For $ZrO_2$, a preferred binary reaction sequence is $$\text{M-Z-H*} + ZrCl_4 \rightarrow \text{M-Z-ZrCl}_3\text{*} + \text{HCl} \tag{A3}$$

$$\text{M-Z-ZrCl*} + H_2O \rightarrow \text{M-Z-ZrOH*} + \text{HCl} \tag{B3}$$

For $SiO_2$, a preferred binary reaction sequence is $$\text{M-Z-H*} + SiCl_4 \rightarrow \text{M-Z-SiCl}_3\text{*} + \text{HCl} \tag{A4}$$

$$\text{M-Z-SiCl*} + H_2O \rightarrow \text{M-Z-SiOH*} + \text{HCl} \tag{B4}$$

Binary reactions of the general type described by equations A1 and B1, where $M^1$ is silicon, are described more fully in J. W. Klaus et al, "Atomic Layer Controlled Growth of $SiO_2$ Films Using Binary Reaction Sequence Chemistry", *Appl. Phys. Lett.* 70, 1092 (1997) and O. Sheh et al., "Atomic Layer Growth of $SiO_2$ on Si(100) and $H_2O$ using a Binary Reaction Sequence", *Surface Science* 334, 135 (1995), both incorporated herein by reference. Analogous reactions for the deposition of other metal oxides such as $ZrO_2$ and $TiO_2$ are described in Tsapatsis et al. (1991) *Ind. Eng. Chem. Res.* 30:2152-2159 and Lin et al., (1992), *AlChE Journal* 38:445-454, both incorporated herein by reference.

Another binary reaction sequence for producing $ZrO_2$ uses tetradiethylaminozirconium and water as reagents, as follows:

$$\text{MOH*} + Zr[N(CH_2CH_3)_2]_4 \rightarrow$$
$$\text{MO—Zr}[N(CH_2CH_3)_2]_3\text{*} + HN(CH_2CH_3)_2 \tag{A5}$$

$$\text{MO—ZrN}(CH_2CH_3)_2\text{*} + H_2O \rightarrow \text{MO—ZrOH*} + HN(CH_2CH_3)_2 \tag{B5}$$

In addition, catalyzed binary reaction techniques such as described in U.S. Pat. No. 6,090,442, entitled "Method of Growing Films on Substrates at Room Temperatures Using Catalyzed Binary Reaction Sequence Chemistry", incorporated by reference, are suitable for producing coatings, especially oxide, nitride or sulfide coatings, most preferably oxide coatings. Reactions of this type can be represented as follows:

$$\text{M-F}_1 + C_1 \rightarrow \text{M-F}_1 \ldots C_1 \tag{A6a}$$

$$\text{M-F}_1 \ldots C_1 + F_2\text{-}M^1\text{-F}_2 \rightarrow \text{M-}M^1\text{-F}_2 + F_1\text{-F}_2 + C_1 \tag{A6b}$$

$$\text{M-}M^1\text{-F}_2 + C_2 \rightarrow \text{M-}M^1\text{-F}_1 \ldots C_2 \tag{B6a}$$

$$\text{M-}M^1\text{-F}_1 \ldots C_2 + F_1\text{-M-F}_1 \rightarrow \text{M-}M^1\text{-M-F}_1 + F_1\text{-F}_2 + C_2 \tag{B6b}$$

$C_1$ and $C_2$ represent catalysts for the A6b and B6b reactions, and may be the same or different. $F_1$ and $F_2$ represent functional groups, and M and $M^1$ are as defined before, and can be the same or different. Reactions A6a and A6b together constitute the first part of a binary reaction sequence, and reactions B6a and B6b together constitute the second half of the binary reaction sequence. An example of such a catalyzed binary reaction sequence for producing $SiO_2$ coatings is:

$$\text{Si—OH*(particle)} + C_5H_5N \rightarrow \text{Si—OH} \ldots C_5H_5N\text{*} \tag{A7a}$$

$$\text{Si—OH} \ldots C_5H_5N\text{*} + SiCl_4 \rightarrow \text{Si—O—SiCl}_3\text{*} + C_5H_5N + HCl \tag{A7b}$$

$$\text{Si—O—SiCl}_3\text{*} + C_5H_5N \rightarrow \text{Si—O—SiCl}_3 \ldots C_5H_5N\text{*} \tag{B7a}$$

$$\text{Si—O—SiCl}_3 \ldots C_5H_5N\text{*} + H_2O \rightarrow \text{Si—O—SiOH*} + C_5H_5N + HCl \tag{B7b}$$

where the asterisks (*) again denote atoms at the surface of the particle. $C_5H_5N$ is the catalyst for each half-reaction in this sequence. This general method is also applicable to forming various $ZrO_2$ and $TiO_2$ coatings.

Except for the catalyzed reaction scheme described above, the binary reactions are generally performed at elevated temperatures, preferably from about 400-1000K, although in some instances reaction temperatures as low at approximately 290K can be used. Preferred temperatures are from about 400-700K. When depositing $ZrO_2$, or coating an underlying $ZrO_2$ surface, reaction temperatures are preferably maintained below about 700K, especially below about 600K, in order to avoid forming large $ZrO_2$ crystallites (i.e., those larger than about 350 nm). It is preferred to employ temperature conditions that substantially prevent the formation of $ZrO_2$ crystallites of greater than about 50 nm.

Between reactions, the particles are subjected to conditions sufficient to remove reaction products and unreacted reagents. This can be done, for example, by subjecting the particles to a high vacuum, such as about $10^{-5}$ Torr or less, after each reaction step. Another method of accomplishing this, which is more readily applicable for industrial application, is to sweep the particles with an inert purge gas between the reaction steps. This purge gas can also act as a fluidizing medium for the particles and as a carrier for the reagents.

Several techniques are useful for monitoring the progress of the reaction. For example, vibrational spectroscopic studies can be performed on high surface area silica powders using transmission Fourier transform infrared techniques. The deposited coatings can be examined using in situ spectroscopic ellipsometry. Atomic force microscopy studies can be used to characterize the roughness of the coating relative to that of the surface of the substrate. X-ray photoelectron spectroscopy and x-ray diffraction can by used to do depth-profiling and ascertain the crystallographic structure of the coating.

Suitable substrate particles include silica particles having average particle sizes within the ranges described before for the base particles. The particles are preferably of amorphous silica. Nanosized silica particles are commercially available under the tradenames Aerosil™ OX50, OX100, OX 150 and OX 200 from DeGussa AG and Cab-O-Sil™ M5 from Cabot Corporation. These particles are typically produced by wet chemistry synthetic pathways. A preferred silica nanoparticle is synthesized by oxidation of hexamethyldisiloxane (HMDSO) in methane/oxygen diffusion flames. Particle size is controlled via control of flow rates. Such silica particles are described by S. E. Pratsinis & S. V. R. Mastrangelo, "Material Synthesis in Aerosol Reactors", *Chemical Engineering Progress* 85, 62-66 (1989) and by R. Mueller, A. Vital, H. Kammler, S. Pratsinis, G. Beaucage & P. Burtscher, "Non-Agglomerated Fumed Silica", *Powder Technology*, (2004) (In Press).

Suitable nano-sized $TiO_2$ particles are commercially available from Du Pont Titanium Technologies, Nanophase Technologies, Inc. (Romeroville, Ill.) and Degussa AG. An example of a suitable nano-sized $TiO_2$ particle is Degussa Aeroxide™P25. NanoProducts Corporation (Longmont, Colo.) supplies a nano-sized $ZrO_2$ particle under the tradename Pürenano™ that is suitable for use as the base particle.

The particles of the invention can be used in dental composites in the same manner as conventional particles. The particles are compounded into a suitable resin at levels of from about 20-90, preferably from about 30-80, especially from about 40-75 volume percent of the mixture, and are conveniently used in conventional manner. The refractive index of the particles is preferably matched to that of the resin to within about 0.025, preferably to within about 0.01, especially to within about 0.005 of each other. Application and curing in the oral environment is not significantly different than for conventional composites based on conventionally prepared particles having similar chemical compositions similar and similar resins.

The resins typically used for dental applications are generally polymerizable and have sufficient strength, hydrolytic stability and non-toxicity to render them suitable for an oral environment. Suitable such resins are described, for example, in U.S. Pat. Nos. 3,066,112, 3,539,533, 3,629,187, 3,709,866, 3,766,132, 3,860,556, 4.002,669, 4,115,346, 4,259,117, 4,292,029, 4,308,190, 4,327,014, 4,379,695, 4,404,150, and 4,503,169. Preferred resins have photocurable (UV- and/or visible light cure) acrylate or methacrylate groups. Examples of such resins include the diglycidylmethacrylate of bisphenol A (BIS-GMA), dodecanediol dimethacrylate, ethyoxylated bisphenol A dimethacrylate, triethyleneglycol dimethacrylate (TEGDMA) or a urethane dimethacrylate (UDMA). Fluorinated monomeric and oligomeric urethane acrylates as well as spiroorthocarbonate monomers and oligomers are also useful.

It is within the scope of the invention to use mixtures of coated particles as described above and uncoated silica particles. In this embodiment, the coated particles are made having a somewhat higher refractive index than the target. These are blended with the silica particles so that the composite refractive index of the blend is at the desired value. To avoid light scattering, the silica particles in such an embodiment are below 350 nanometers in diameter, preferably below 250 nanometers in diameter and more preferably below 100 nanometers in diameter and especially from about 10-80 nanometers in diameter. Provided that all particles have sizes well below the wavelength of visible light, and provided that the particles are very well blended, the refractive index of these blends will be a function of the volume fractions of the various materials contained in the individual particles, as described before.

The following examples are provided to illustrate coating processes applicable to making the particles of the invention. These examples are not intended to limit the scope of the inventions. All parts and percentages are by weight unless otherwise indicated.

EXAMPLE 1

Deposition of a $TiO_2$ Layer Over $ZrO_2$ Particles $ZrO_2$ particles are coated with $TiO_2$ in a vacuum apparatus designed for in situ transmission FTIR vibrational spectroscopy studies. The vacuum chamber consists of two chambers separated by a gate valve. The upper chamber is equipped with a capacitance manometer and several leak valves for controlling the reactant exposures. This chamber is used for the FTIR studies. The lower chamber contains an ion gauge and a Dycor quadru-pole mass spectrometer. High vacuum is achieved by using a 200 L/s turbomolecular pump located in the lower chamber. $ZrO_2$ particles having a surface area of 20.2 $m^2/g$ and a diameter of 50 nm are obtained from Nanomaterials Research Corporation (Longmont, Colo.). $TiCl_4$ (99.999%) and $H_2O$ (HPLC grade) are obtained from Alfa Aesar and Fisher Scientific, respectively. Both reactants are dispensed into the chamber from glass bulbs. The $ZrO_2$ particles are pressed into a tungsten grid using polished stainless steel dies and a manual press. The grid has dimensions of approximately 2 cm×3 cm with a thickness of 0.002 inch and 100 lines per inch. A tantalum foil is spot-welded to each side of the grid to facilitate resistive heating. A chromel-alumel thermocouple is used to monitor accurately the sample temperature. A Remco (Type 552) ceramic adhesive is used to attach the thermocouple to the upper center of the tungsten grid. The tungsten grid is held between two copper clamps attached to an x-y-z rotary manipulator. The x-y-z adjustment capabilities of the manipulator facilitate optimum alignment of the $ZrO_2$ sample in the infrared beam. The manipulator also contains the current and thermocouple feedthroughs necessary for sample heating and temperature regulation. Sample temperatures between 300 and 1150 K can be achieved and maintained without the use of liquid nitrogen in the cryostat of the manipulator.

During low pressure exposures, the reactants are introduced into the upper chamber with the gate valve open between the upper and lower chambers. The gate valve to the turbomolecular pump can be partially throttled during these exposures to adjust the pumping speed. These low pressure exposures in the range of $1 \times 10^{-4}$ to $1 \times 10^{-3}$ Torr are measured using the ion gauge. For exposures at pressures in the range of 0.01-10 Torr, the reactant gases are introduced into the upper chamber with the gate valve closed between the upper and lower chambers. These pressures are measured using the capacitance manometer. After the exposures, the upper chamber is evacuated using a liquid nitrogen trap backed by a mechanical pump. To further reduce the chamber pressure, the gate valve is opened to the lower chamber and turbomolecular pump. The base pressure between $TiCl_4$ and $H_2O$ cycles is $5.0 \times 10^{-6}$ Torr.

A Nicolet Magna 560 Fourier transform infrared (FTIR) spectrometer with an MCT-B infrared detector is used to perform the vibrational spectroscopic studies. The infrared beam enters the upper chamber through a 6 mm thick CsI window, passes through the tungsten grid and exits through an identical CsI window before reaching the detector. Gate valves isolate the CsI windows from the chamber during the $TiCl_4$ and $H_2O$ exposures to prevent $TiO_2$ deposition on the windows. All of the spectra are recorded after the chamber was evacuated at a sample temperature of 600 K.

$TiO_2$ coating layers are prepared by exposing the $ZrO_2$ particles alternately to $TiCl_4$ and $H_2O$ at 600K. For the first nine reaction cycles, $TiCl_4$ exposures are $\geq 1.4 \times 10^{10}$L and $H_2O$ exposures are $\geq 7.2 \times 10^{10}$ Langmuir ($10^{-6}$ Torr-sec). Remaining cycles (up to about 40 total) consist of $TiCl_4$ exposures of $5.4 \times 10^9$L and $H_2O$ exposures are $3.6 \times 10^{10}$L.

FTIR analysis of the particle surfaces confirms the disappearance of surface ZrOH groups and the appearance of surface TiOH groups as the $TiCl_4/H_2O$ cycles are repeated. Vibrational frequencies are consistent with a rutile crystalline structure.

The TEM images are obtained with an HRTEM JEOL 2010 high resolution transmission electron microscope in combination with electron dispersive spectroscopy and a GATAN digital micrograph with a slow scan CCD camera. These TEM images show that after 40 reaction cycles, a conformal $TiO_2$ coating with a thickness of ~17 angstroms encapsulates the base particles, without particle agglomeration. This is consistent with a $TiO_2$ growth rate of ~0.4A/cycle. The film shows some roughness and appears to be fairly amorphous. This apparent amorphous structure may be due to the very small layer thickness suppressing the visualization of pronounced $TiO_2$ crystallinity.

EXAMPLE 2

Process for Depositing $TiO_2$ and $ZrO_2$ Layers On Silica Particles

~12 nm fumed $SiO_2$ particles (Aerosil 200tM, from DeGussa) are fluidized at $3u_{mf}$ using $N_2$ as a fluidizing gas. The fluidized bed is 5.1 cm in diameter and 91.4 cm long. The reactor itself is composed of stainless steel and is encased by a clamshell-type furnace. Separate reactant bubblers for each of the reagents are attached to the system via their vent lines, and are operated by the driving force of their vapor pressures. Two sets of solenoid valves allow the reagents to be sequentially dosed into the system. The fluidizing gas flow is maintained using a mass flow controller from MKS instruments. An additional mass flow controller controls a separate purge flow through the dosing lines. The dosing line entrance into the reactor is just beneath a removable porous metal fluidized bed distributor plate. With the fluidizing gas, each dosing reagent can be pulsed into the system and then purged with $N_2$ to remove it from the system prior to the next dose of the other reactant. In this manner, ALD sequential surface chemistry is easily carried out and undesirable CVD (chemical vapor deposition) is avoided. The reactor itself is maintained at low pressure near vacuum using a large (Alcatel 2063AC) pump, and the dosing lines can also be pumped down using smaller (Alcatel 2008a) separate vacuum pumps. The reaction sequence can be carried out between 500 and 700 K. Approximately 50 g of $SiO_2$ particles are processed for each run.

A $TiO_2$ layer is introduced onto the silica particles using $TiCl_4$ and water as dosing reagents. Separate samples of silica particles are treated with 10, 20, 40 and 80 cycles, respectively of the $TiCl_4/H_2O$ reaction cycles to form, respectively, 1, 2, 4 and 8 nm-thick $TiO_2$ coating layers on the silica particles. The thickness of the $TiO_2$ layer significantly impacts the refractive index and, hence, the translucency of the particles. Particles having a 1 nm $TiO_2$ layer have a calculated refractive index of approximately 1.992. Those having 2 nm, 4 nm and 8 nm $TiO_2$ layers have calculated refractive indices of about 2.292, 2.588 and 2.785, respectively.

A $ZrO_2$ layer is deposited on top of the $TiO_2$ layers on the resulting particles, using $ZrCl_4$ and water as dosing reagents. The $ZrO_2$ layer creates a smaller change in refractive index, and provides a hard and x-ray opaque shell.

What is claimed is:

1. A material in the form of particles, the particles comprising a silica base particle and one or more $ZrO_2$ and $TiO_2$ coating layers deposited by an atomic layer deposition process on the surface of said base particle, wherein the particles have a predetermined refractive index greater than that of silica alone, an average diameter of from 10 to 150 nanometers, at least one $TiO_2$ layer deposited by an atomic layer deposition process upon the silica base particle and at least one $ZrO_2$ layer deposited by an atomic layer deposition process upon the surface of a $TiO_2$ layer, wherein the material has a refractive index of 1.48 to 1.60.

2. The material of claim 1 wherein at least one $SiO_2$ layer deposited by an atomic layer deposition process is present upon the surface of the $ZrO_2$ layer.

3. A curable dental composite material comprising a photocurable polymeric resin and a particulate filler material, wherein the particulate filler material is a material having a refractive index in the range of about 1.50 to about 1.58 and an average diameter of up to about 350 nanometers, the filler material comprising a silica base particle having an average diameter of up to about 300 nanometers containing at least one $ZrO_2$ or $TiO_2$ layer deposited by an atomic layer deposition process, wherein the particle has a predetermined refractive index greater than that of silica alone and the refractive index of the particles is within 0.01 unit of the refractive index of the resin.

4. The curable dental composite material of claim 3, wherein the particles have at least one $SiO_2$ layer deposited by an atomic layer deposition process upon the surface of a $ZrO_2$ or $TiO_2$ layer.

5. The curable dental composite material of claim 3, wherein the particles have at least one $TiO_2$ layer deposited by an atomic layer deposition process upon the silica base particle.

6. The curable dental composite material of claim 5, wherein the particles have at least one $ZrO_2$ layer deposited by an atomic layer deposition process upon the surface of a $TiO_2$ layer.

7. The curable dental composite material of claim 3 wherein the resin is a diglycidylmethacrylate of bisphenol A (BIS-GMA), dodecanediol dimethacrylate, ethyoxylated bisphenol A dimethacrylate, triethyleneglycol dimethacrylate (TEGDMA), urethane dimethacrylate (UDMA), fluorinated monomeric or oligomeric urethane acrylate or a spiroorthocarbonate monomers or oligomers.

* * * * *